United States Patent [19]

McRae

[11] Plant 4,932

[45] Nov. 9, 1982

[54] LILY PLANT: LILIUM 'VENTURE'

[75] Inventor: Edward A. McRae, Boring, Oreg.

[73] Assignee: Melridge, Inc., Sandy, Oreg.

[21] Appl. No.: 258,741

[22] Filed: Apr. 29, 1981

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—Eugene D. Farley

[57] ABSTRACT

A new variety of Asiatic hybrid lily plant bearing large clusters of large flowers of excellent form, distinctive color, and long persistence, both on the plant and as cut flowers. The plant is characterized by its vigorous growth, its rapid natural propagation under field conditions, its healthy growth when forced under glass throughout the entire year, its favorable bulb growth response under prolonged storage even when the bulbs are frozen, its tall stems, its high bud count and the deep blood red color of its buds and flowers.

1 Drawing Figure

BACKGROUND AND GENERAL STATEMENT OF THE INVENTION

My new variety of lily is classified botanically as a Lilium hybrid; commercially as an upright Asiatic hybrid, Division I-A in the horticultural classification of the genus Lilium adopted by the Royal Horticultural Society of London.

My new variety of lily plant originated as a seedling selected from a group of seedlings among the seedling beds of test crosses of Oregon Bulb Farms at Sandy, Oreg. The cross was made in 1969 and the lily plant first flowered in 1971.

The cross was made during a breeding program having as its objective the production of brilliantly-colored, upright-flowering lily cultivars which would perform well when forced into flower under glass throughout the year, in addition to meeting the requirements of vigor, disease resistance, and rapid natural propagation in field growth. Cultivars were sought which would be disease resistant, virus tolerant, and not susceptible to leaf scorch or bud abortion when forced under glass.

The cross was made between the seed parent Lilium 'Tabasco' (unpatented) and the pollen parent Lilium 'Connecticut Red' (unpatented).

My new lily plant, Lilium 'Venture' is characterized by its vigorous growth, its rapid natural propagation under field conditions, its healthy and vigorous growth when forced under glass throughout the entire year, its favorable growth response after prolonged storage even when the bulbs are frozen, its tall stems, its high bud count, and the deep blood red color of its buds and flowers.

My new flower plant Lilium 'Venture' most closely resembles the older cultivar 'Showboat' (U.S. Plant Pat. No. 4,177). However, its flower color is slightly lighter. It is superior to 'Showboat' in that it has taller stems and a higher bud count. It accordingly is much more useful as a cut flower cultivar.

My new variety of lily plant has been asexually reproduced by me and under my direction at Oregon Bulb Farms, Sandy, Oreg. Successive generations produced by bulb scale propagation and by natural, below-ground stem bulblet production have demonstrated that the novel and distinctive characteristics of my new variety are fixed and hold true under asexual propagation from generation to generation.

THE DRAWING

My new variety of lily plant is illustrated on the accompanying photographic rendering which shows the plant, its foliage, and its buds in their various stages of development and the open bloom in full color.

DESCRIPTION OF THE NEW VARIETY

The following is a detailed description of my new variety of Asiatic hybrid lily, with nomenclature according to *The International Lily Register* (Royal Horticultural Society, London, Second Edition, 1969) and with color designations according to the Royal Horticultural Society Color Chart, published by the Royal Horticultural Society in 1966.

THE PLANT

Form: Bulbous monocotyledon.
Height: 85–120 cm (31–48").
Growth: Vigorous, with considerable strength.
Foliage:

*Quantity.*—Abundant, about 80–100 leaves per stem.
*Size of leaves.*—9–10 cm (3–3½") long and 0.6–0.8 (¼–⅜") wide.
*Shape of leaves.*—Lanceolate.
*Texture of leaves.*—Leaves entire (not serrated), margins and axils lightly pubescent.
*Color of leaves, upperside.*—Medium green.
*Color of leaves, underside.*—Medium green.
*Ribs and veins of leaves.*—Typical monocotyledonous venation; light green parallel veins.

INFLORESCENCE

Well-spaced pyramidal raceme with no secondary buds. Bulbs 10–12 cm in circumference produce an average of 9–10 buds; bulbs 12–15 cm in circumference produce 11–12 flowers.
Peduncle and pedicels: Lightly hairy.
Strength of inflorescence: Strong and wirey.
Color of inflorescence: Stems reddish.

THE BUDS

Size: 7.0–8.5 cm (3–3⅓") long, 2–4 cm (¾–1¼") wide.
Form: Lanceolate with obtuse tip; typical of Asiatic lilies.

Opens slowly: Opens in about 1 hour in response to morning light; flowers further up the stem open on subsequent days over an interval of 1-2 weeks. Typical of Asiatic lilies.

THE FLOWER

Blooms: Late June or early July in western Oregon, in midseason once, and profusely.

Size: Flower diameter is 15-18 cm (6-7"). Inner tepals are 2.9-3.2 cm (1-1¼") wide. Outer tepals are 2.2-2.5 cm (⅞-1") wide.

Shape when bloom first opens: Bowl-shaped with recurving tips. Tepals recurve more as flower ages.

Tepal arrangement: Typical of the genus Lilium, with 6 entire, imbricated tepals.

*Color, outer tepal.*—Deep blood red (Royal Horticultural Society's Horticultural Color Code #820/1).

*Color, base of tepals.*—Currant red (RHS HCC #821).

*Color, inner tepal.*—Deep blood red (RHS HCC #820/1).

*Color, reverse of tepals.*—Deep blood red (RHS HCC #820/1).

Tepal duration: Tepals remain on individual flowers 5-7 days, stem has flowers with tepals adhering for about 3 weeks. Tepals fall as flower ages.

Flower texture: Shiny, velvety. Not affected by hot or wet weather although intensity of color may be reduced by hot weather.

Pedicel: Sturdy and wirey; slightly ascending.

*Length.*—5-7 cm (2-3").

*Color.*—Reddish, lightly pubescent.

Disease resistance: To Botrytis blight and to Fusarium bulb rot.

Fragrance: None.

Lasting quality: Flowers remain on plants for about 3-4 weeks. Flowers remain on cut-flower stems for about 3 weeks, with adequate light.

THE REPRODUCTIVE ORGANS

Stamens and anthers: Typical of genus Lilium. 6 Versatile anthers hang (singly) from 6 filaments.

Filaments: 5-6 cm (2") long and light red.

Pollen: Deep golden brown.

Pistil: 1, typical of genus Lilium. Style is 5-6 cm (2") long.

Stigma: Tiny, three-lobed, dark plum in color, velvety texture.

Ovary: Typical of genus Lilium. Superior, single, 6-chambered ovary.

THE FRUIT

Fertile, an ovoid to oblong capsule with 6 chambers.

Color at maturity: Medium green overlaid with purple; fades to soft brown when fruit splits open to release seeds.

THE BULBS

Color of bulbs: White.

Size of bulbs: Usual commercial size is 12-20 cm (5-8") in circumference; bulbs can reach much larger size if desired.

I claim:

1. A new and distinctive variety of Asiatic hybrid lily plant substantially as herein shown and described, characterized by its vigorous growth, its rapid natural propagation under field conditions, its healthy growth when forced under glass throughout the entire year, its favorable bulb growth response after prolonged storage even when the bulbs are frozen, its tall stems, its high bud count, and the deep, blood red color of its buds and flowers.

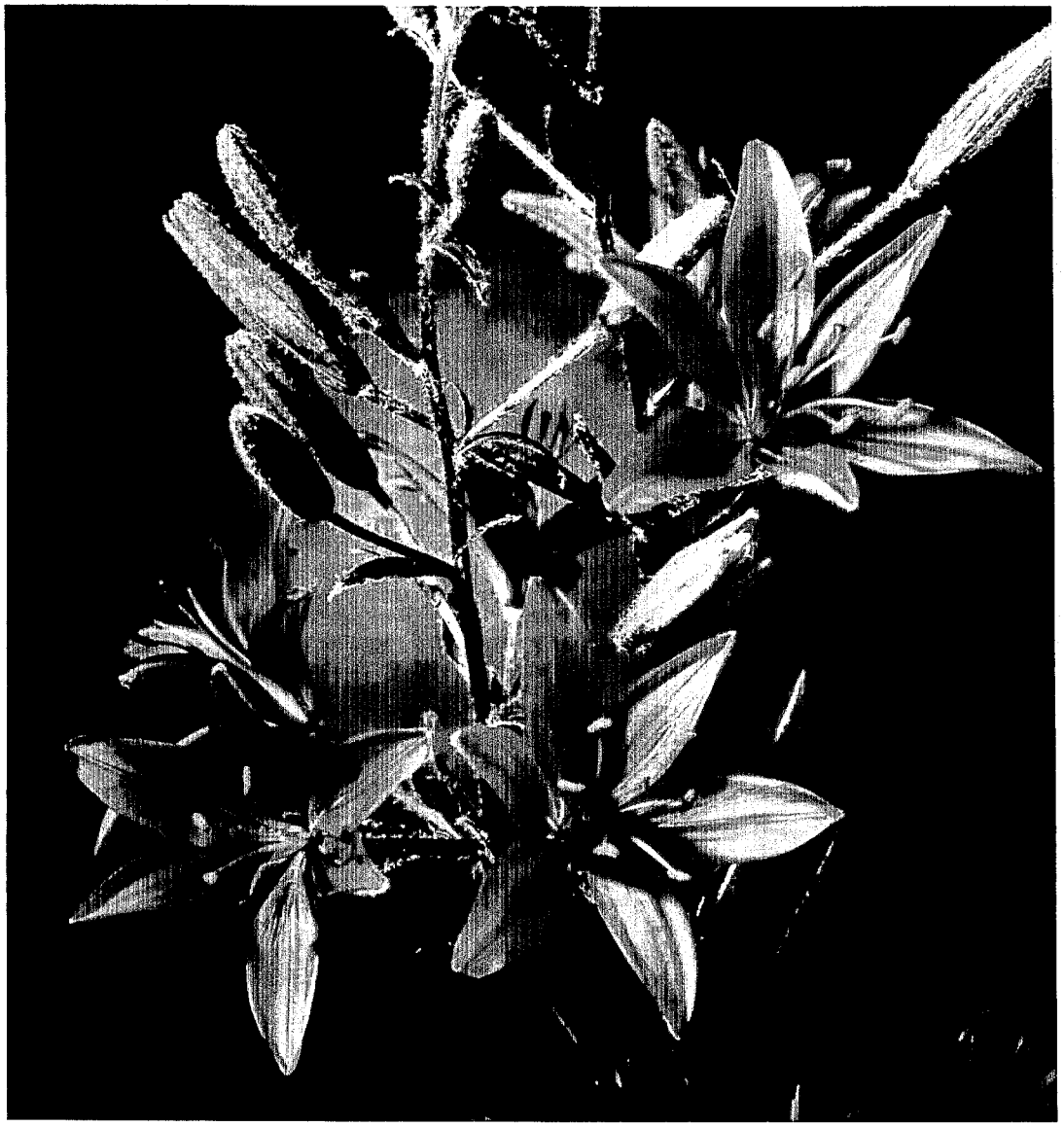

* * * * *